United States Patent
Gross et al.

[11] Patent Number: 5,997,501
[45] Date of Patent: Dec. 7, 1999

[54] INTRADERMAL DRUG DELIVERY DEVICE

[75] Inventors: Joseph Gross; John Gerard Kelly, both of Dublin, Ireland

[73] Assignee: Elan Corporation, plc, Dublin, Ireland

[21] Appl. No.: 08/647,954

[22] PCT Filed: Nov. 17, 1994

[86] PCT No.: PCT/IE94/00055

§ 371 Date: Aug. 19, 1996

§ 102(e) Date: Aug. 19, 1996

[87] PCT Pub. No.: WO95/13838

PCT Pub. Date: May 26, 1995

[30] Foreign Application Priority Data

Nov. 18, 1993 [IE] Ireland ..................... 930882

[51] Int. Cl.[6] .................................................. A61M 31/00
[52] U.S. Cl. .................................................. 604/65
[58] Field of Search .................... 604/890.1, 891.1, 604/30, 31, 50, 65–67; 128/DIG. 12, DIG. 13

[56] References Cited

U.S. PATENT DOCUMENTS

| | | | |
|---|---|---|---|
| 2,408,323 | 9/1946 | Lockhart et al. | 128/220 |
| 2,576,951 | 12/1951 | Lockhart et al. | 128/218 |
| 3,923,060 | 12/1975 | Ellinwood et al. | 128/260 |
| 4,140,117 | 2/1979 | Buckles et al. | 128/213 |
| 4,522,622 | 6/1985 | Peery et al. | 604/191 |
| 4,627,445 | 12/1986 | Garcia et al. | 128/770 |
| 4,637,403 | 1/1987 | Garcia et al. | 128/770 |
| 4,684,365 | 8/1987 | Reinicke | 604/126 |
| 4,697,622 | 10/1987 | Swift et al. | 141/1 |
| 4,734,092 | 3/1988 | Millerd | 604/67 |
| 4,753,651 | 6/1988 | Eckenhoff | 424/449 |
| 4,886,499 | 12/1989 | Cirelli et al. | 604/131 |
| 4,894,054 | 1/1990 | Miskinyar | 604/136 |
| 4,902,278 | 2/1990 | Maget et al. | 604/132 |
| 5,070,886 | 12/1991 | Mitchen et al. | 128/771 |
| 5,079,421 | 1/1992 | Knudson et al. | 250/343 |
| 5,090,963 | 2/1992 | Gross et al. | 604/132 |
| 5,156,591 | 10/1992 | Gross et al. | 604/20 |
| 5,279,544 | 1/1994 | Gross et al. | 604/20 |
| 5,318,557 | 6/1994 | Gross | 604/891.1 |
| 5,354,264 | 10/1994 | Bae et al. | 604/21 |
| 5,390,671 | 2/1995 | Lord et al. | 128/635 |
| 5,527,287 | 6/1996 | Miskinyar | 604/135 |
| 5,545,143 | 8/1996 | Fischell | 604/180 |
| 5,562,613 | 10/1996 | Kaldany | 604/57 |

FOREIGN PATENT DOCUMENTS

| | | | |
|---|---|---|---|
| 0 098 592 | 1/1984 | European Pat. Off. | A61M 5/00 |
| 0 209 677 | 1/1987 | European Pat. Off. | A61M 5/14 |
| 0 258 073 A1 | 2/1988 | European Pat. Off. | A61M 5/20 |
| 0 401 179 | 12/1990 | European Pat. Off. | A61B 5/00 |
| 0 513 879 A2 | 11/1992 | European Pat. Off. | A61M 37/00 |

(List continued on next page.)

*Primary Examiner*—Manuel Mendez
*Attorney, Agent, or Firm*—Kathleen L. Maher

[57] ABSTRACT

An intradermal drug delivery device comprises a housing (301a, 301b) having a drug reservoir (312) therewithin and a gas generation chamber (313) separated from the reservoir (312) by a displaceable membrane (311). A microprocessor-controlled electrolytic cell (316a, 316b, 319) provides gas to expand the gas generation chamber (313) and thereby contract the reservoir (312). A hollow needle (310), communicating at an inner end thereof with the reservoir (312), extends from a lower surface (308) of the housing (301) such that contraction of the reservoir (312) forces drug to escape therefrom via the needle (310). The device permits delivery of drugs of relatively large molecular weights at slow controllable rates. A displaceable protective cover (303) is mounted in means (307) allowing movement of the cover (303) between extended and retracted positions (305, 306). The cover (303) has an adhesive lower surface (309) for attachment to the skin of a subject. In use, a release liner is removed, the device is pressed against the skin and the cover (303) snaps back to the retracted position (306), the needle (310) thereby piercing the skin. After use the housing (301) is pulled away and the cover (303) snaps to the extended position (306) before detaching from the skin, thus concealing the needle (310) before disposal.

41 Claims, 11 Drawing Sheets

FOREIGN PATENT DOCUMENTS

| | | |
|---|---|---|
| 0 315 656 B1 | 7/1993 | European Pat. Off. .......... A61M 5/14 |
| 0 652 027 A1 | 10/1995 | European Pat. Off. ....... A61M 25/06 |
| 0 589 356 B1 | 11/1998 | European Pat. Off. ....... A61M 5/145 |
| 60868 | 8/1994 | Switzerland ..................... A61M 5/20 |
| 2 094 628 | 9/1982 | United Kingdom ............ A61M 5/20 |
| 2 050 843 | 9/1983 | United Kingdom ............ A61M 5/20 |
| 2 140 309 | 6/1986 | United Kingdom ............ A61M 5/14 |
| 2 131 496 | 10/1986 | United Kingdom ............ F04B 43/00 |
| 2 146 460 | 6/1987 | United Kingdom ............ A61M 5/20 |
| 2 221 394 | 4/1992 | United Kingdom .......... A61M 37/00 |
| WO-89/12473 | 12/1989 | WIPO ............................. A61M 5/20 |
| WO-91/00753 | 1/1991 | WIPO ............................. A61M 31/00 |
| WO-92/11879 | 7/1992 | WIPO ............................. A61M 1/08 |
| WO 93/07920 | 4/1993 | WIPO ............................. A61M 5/155 |
| WO-93/17754 | 9/1993 | WIPO .............................. A61N 1/30 |
| WO 93/21987 | 11/1993 | WIPO ............................. A61M 37/00 |
| WO 94/27669 | 8/1994 | WIPO ............................. A61M 37/00 |
| WO 95/10223 | 4/1995 | WIPO ............................... A61B 5/00 |
| WO 95/15191 | 8/1995 | WIPO ............................. A61M 37/00 |
| WO 96/25089 | 8/1996 | WIPO ............................... A61B 5/00 |

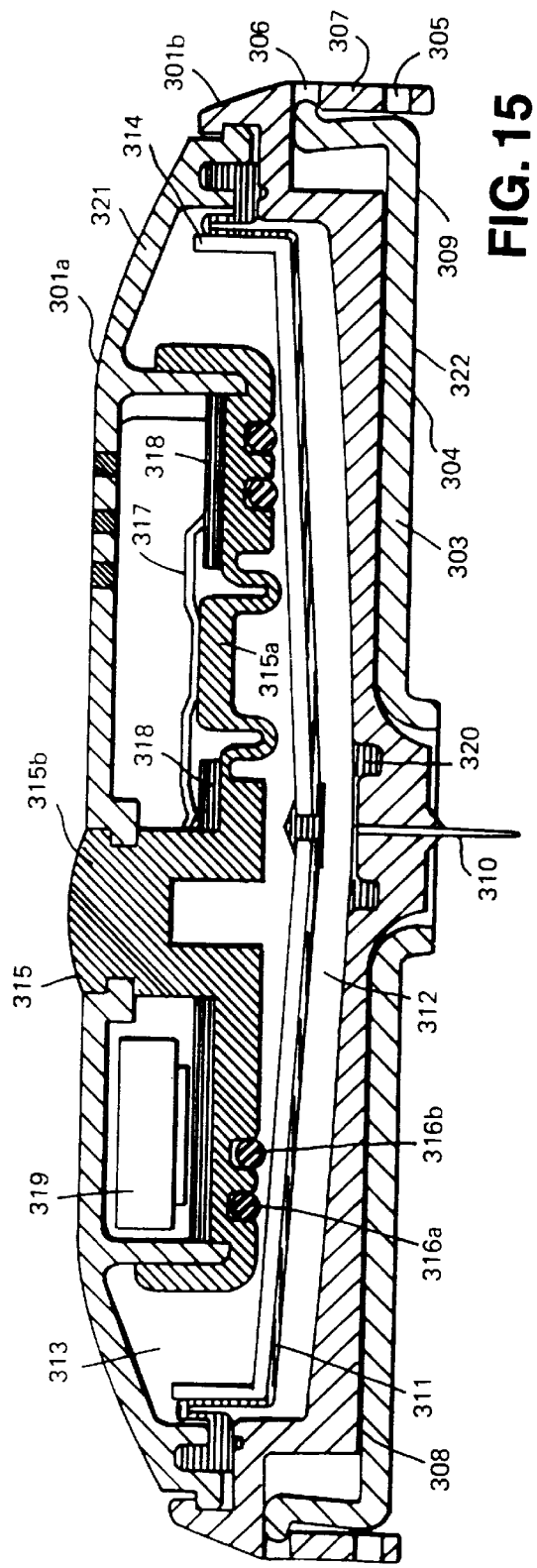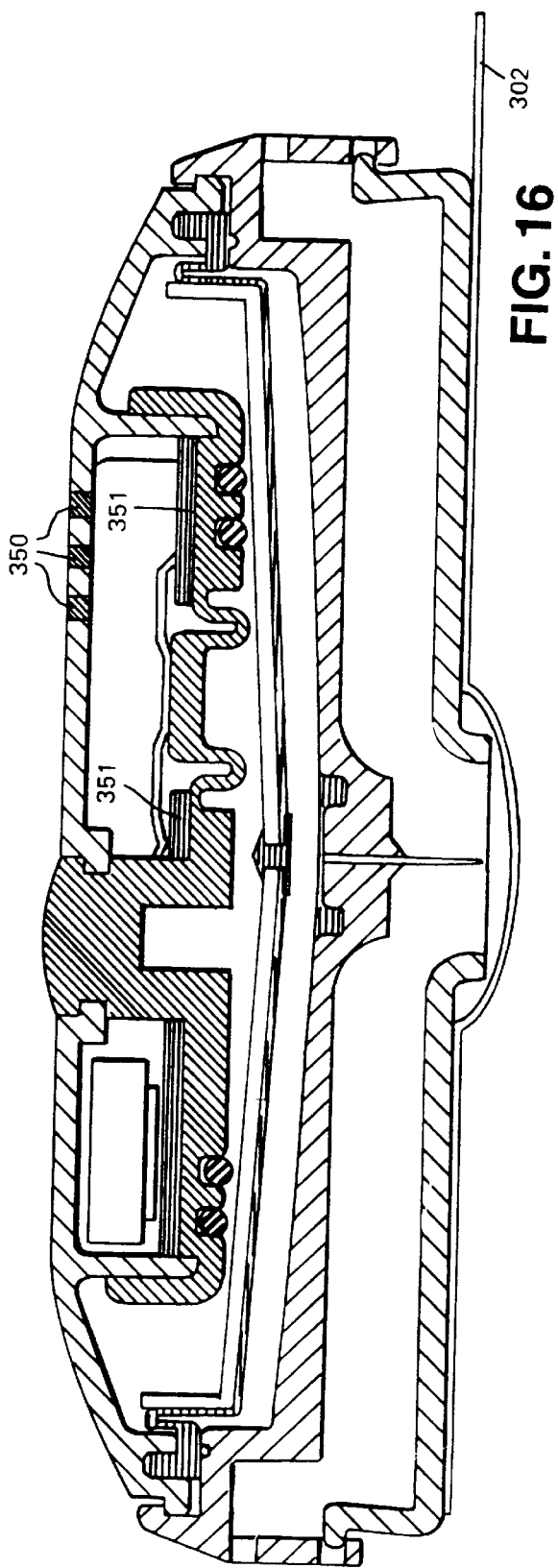

INTRADERMAL DRUG DELIVERY DEVICE

TECHNICAL FIELD

The present invention relates to drug delivery devices, and in particular to an intradermal drug delivery device for delivering a liquid drug to a subject via the subject's skin.

BACKGROUND ART

One type of transdermal drug delivery device is in the form of a patch applied to the subject's skin and containing drug penetrating the skin by osmosis and/or by a controlled mass transport phenomenon such as iontophoresis. Simple patches, however, provide no control, or limited control, of the rate of drug delivery, which depends on skin conditions, the nature (particularly molecular size) of the drug to be delivered, and the like. Iontophoretic devices are also not entirely satisfactory in their ability to deliver large molecules and to control the rate of delivery thereof. All such devices are limited by the barrier function of the skin.

Another transdermal drug delivery device is described in International Patent Publication WO 93/17754. In one embodiment this device comprises a housing containing a liquid reservoir and a drug delivery body carried by the housing and engageable with the subject's skin. The drug delivery body carries a plurality of hollow needles (of which there are preferably at least fifty) having an outer diameter of the order of 1 mm, which needles are designed to pierce the outer layer of dead cells (the stratum corneum) of the skin, thereby enhancing the penetration of the drug through the skin.

However, certain disadvantages are associated with this method of drug delivery. Firstly, there is a risk of considerable pain and traumatisation of the skin associated with the application of the particular array of needles. Secondly, the drug may leak out around the entry point of each needle as a result of the pressure being applied to assist the delivery of the drug. A film of liquid drug covering the area of application may cause irritation for subjects with sensitive skin; certain drugs may aggravate this irritation. The leakage also results in a lower efficiency of drug delivery. Thirdly, it can be difficult to ensure that the device is correctly applied with the tips of the needles penetrating the strateum corneum. The skin has a natural resilience and elasticity. The device is pressed onto the skin such that the entire area of the needle arrangement depresses the surface of the skin, even when considerable pressure is applied. For this reason, an extra degree of pain is associated with the correct application of the device due to the amount of force needed to properly pierce the stratum corneum with all of the needles.

DISCLOSURE OF INVENTION

According to the present invention, there is provided an intradermal drug delivery device for delivering at least one liquid drug to a subject via the subject's skin, comprising: a housing having a lower surface for application to the skin of the subject; means for affixing the housing in position with the lower surface in contact with the subject's skin; a drug reservoir within the housing; a single hollow needle associated with the drug reservoir extending through the lower surface, having an inner end communicating with the drug reservoir and an outer end projecting outwards a sufficient distance so as to penetrate through the epidermis and into the dermis when the housing is pressed against the skin; and means for actively discharging the drug from the reservoir to the subject's skin via the needle; the lower surface being shaped such that when it is pressed against the skin, a substantial proportion of the pressure applied to the skin is directed through the needle tip; and the needle having an outer diameter of 0.5 mm or less, preferably 0.2 mm or less.

Also, according to the present invention, there is provided an intradermal drug delivery device for the delivery of at least one drug to a subject via the subject's skin, comprising: a housing having a lower surface; a drug reservoir located within the housing; cover mounting means attached to the housing; a protective displaceable cover having an upper surface and a lower surface and capable of being extendibly and retractably engaged in the cover mounting means such that the cover is positioned substantially parallel to the lower surface of the housing and the upper surface of the cover is proximal to the lower surface of the housing when the cover is retracted and the upper surface of the cover is distal to the lower surface of the housing when the cover is extended; means for affixing the cover in position with the lower surface of the cover in contact with the subject's skin; a single hollow needle associated with the drug reservoir and extending through the lower surface of the housing, having an inner end communicating with the drug reservoir and an outer end projecting outwards a sufficient distance so as to extend no further than the upper surface of the cover when the cover is extended and so as to penetrate through the epidermis and into the dermis when the cover is affixed to the subject's skin and retracted, wherein the needle has an outer diameter of 0.5 mm or less, preferably 0.2 mm, or less; and means for actively discharging the drug from the reservoir to the subject's skin via the needle.

According to the preferred embodiments described below, the needle projects outwardly of the housing or, if the device has a protective displaceable cover, outwardly of the protective displaceable cover when the device is affixed to the subject approximately 0.3–5.0 mm, more preferably 0.3–3.0 mm, most preferably 0.3–1.0 mm, and has an outer diameter of 0.075–0.5 mm, most preferably 0.1–0.2 mm and an inner diameter of 0.05–0.3 mm, more preferably 0.05–0.15 mm, most preferably 0.05–0.075 mm.

As will be described more particularly below, such an intradermal drug delivery device permits the delivery of a variety of drugs including drugs of relatively large molecular size, and at slow rates which can be precisely controlled.

According to further features of the invention described below, the drug reservoir may be an expansible-contractible chamber which is expanded upon being filled with the drug and is contracted to dispense the drug therefrom at controlled rates by the means for actively discharging the drug. These means can include an electrically-controlled gas generator, such as an electrolytic cell, a prestressed spring or membrane, or osmotic means to provide for osmosis between a pure water compartment and a saline compartment included within the housing.

According to another aspect of the invention, there is provided a drug delivery device having a plurality of drug reservoirs within the housing, all drug reservoirs communicating with an outlet cavity with which the single hollow needle also communicates, and means such as electrical means for individually controlling the feeding of drug from the plurality of reservoirs to the outlet cavity.

According to further features of the invention described below, the housing can comprise at least two parts: (1) an electronic control unit for controlling the discharge of the drug from the drug reservoir, such as providing for preprogrammed continuous administration of the drug, fully programmable continuous, pulsatile or intermittent administration of the drug and/or patient controlled administration of the drug and (2) a disposable cartridge unit for housing the drug reservoir or reservoirs and/or the means for actively discharging the drug from the reservoir to the subject's skin.

Further features and advantages of the invention will be apparent from the description below.

BRIEF DESCRIPTION OF DRAWINGS

The invention is herein described, by way of example only, with reference to the accompanying drawings, wherein:

FIG. 15 is an enlarged longitudinal sectional view of the device of FIG. 12 in which the protective displaceable cover is retracted;

FIG. 16 is an enlarged longitudinal sectional view illustrating the disposable cartridge unit of a two-part intradermal drug delivery device constructed in accordance with the present invention;

Figure 1:
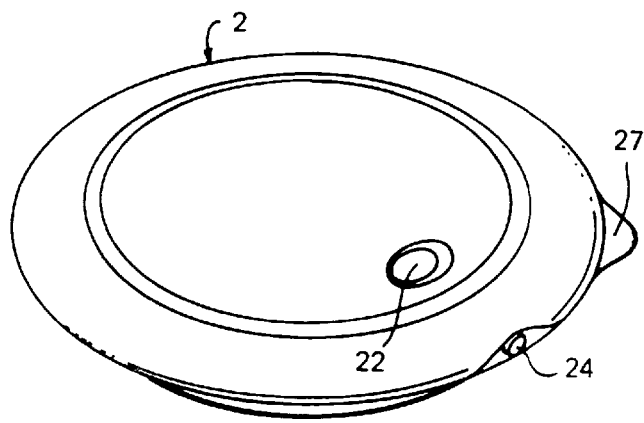
FIG. 1 illustrates one form of an intradermal drug delivery device constructed in accordance with the present invention.

The device according to the invention overcomes the disadvantages indicated above for the following reasons: Firstly, since only a single needle is generally used, only a single point of entry is associated with the application of the device, eliminating most of the pain and trauma resulting from the application of the device. In addition, the extremely narrow diameter of the single needle allows the application to be virtually painless and minimally invasive.

Secondly, the amount of leakage is diminished to a very large extent, if not totally. The delivery is far more controlled as a result. The leakage is reduced for two reasons: (i) the drug is delivered below the epidermis (and not just to below the strateum corneum); and (ii) only a single point exists at which leakage might occur.

Thirdly, the shape of the lower surface results in a substantial proportion of the pressure being directed through the needle tip. If the device is not correctly shaped, too much pressure may be directed through the lower surface so that the skin is stretched by the surface of the device and not the needle. According to the invention, the needle must provide sufficient pressure to stretch and pierce the epidermis, i.e., the elasticity of the skin must be directed against the needle. It should be noted that the effective pressure (force applied to the housing per unit area of skin contact) is, for a given force, far higher for the device according to the invention, since the effective area of application is diminished approximately fifty-fold when only one needle is applied as opposed to 50 needles, and is further reduced as a result of the narrow diameter needle used.

The protective displaceable cover not only protects the needle from damage when the device is not in use but also provides for a safer device in that the needle extends beyond the cover only when the device is in use. Thus, accidental contact with the needle is minimized. Additionally, the displaceable protective cover can be movably positioned so as to allow the needle to project outward from the cover to a preselected multiplicity of different lengths. In this manner, the depth of penetration of the needle can be easily varied to accommodate administration of the device to different parts of the body of the subject or to different thicknesses of skin.

Embodiments having a disposable cartridge unit and a reusable electronic control unit have the advantage of providing reuse of the relatively expensive and/or long-lasting electronic control unit part. The disposable (and replaceable) cartridge unit contains those elements that are exhausted relatively quickly such as the drug or drugs and/or the means for actively discharging the drug from the reservoir to the subject.

Since the intradermal device of this invention delivers the drug below the epidermis, i.e., to the interface between the epidermis and the dermis or to the interior of the dermis or subcutaneously, many of the problems of transdermal application are non-existent; the drug is delivered directly to a capillary-containing tissue and has no barriers to pass through before entering the vascular system.

Preferably, the means for holding the housing or, if the device has a protective displaceable cover, the protective displaceable cover in position comprises a pressure-adhesive coating, such as an acrylate adhesive, on the lower surface thereof. When the device is pressed against the skin, the needle penetrates the epidermis and the pressure-adhesive coating affixes the lower surface to the skin. A single-step, painless and trauma-free application is thus provided by the invention. Additionally or alternatively, the device may be held in position by a strap or bracelet.

According to one embodiment of the invention, the lower surface of the housing or, if the device has a protective displaceable cover, the protective displaceable cover has a convex shape and the hollow needle extends from (or through) the center of the convexity. Alternatively, the lower surface of the housing (or the lower surface of the protective displaceable cover) is provided with a protuberance from which the needle projects. In a further alternative, the lower surface of the housing or cover is of a conical shape and the hollow needle extends from the apex of the cone. In a further embodiment, the lower surface of the housing or cover can have a convex shape and also be provided with a protuberance from which the needle projects.

When the device does not have a protective displaceable cover, the needle is positioned to engage the skin directly so that it pierces the skin before a large part of the surface has made contact. In effect, parts of the surface distal from the needle is held back from the skin as a consequence of the shape of the lower surface. For this reason, much of the pressure which might have been applied by the surface of a flat device is instead directed through the needle tip.

The device may however have a flat surface provided that the size of the device or the shape and elasticity of the skin to which the device is to he applied enables a substantial portion of the pressure to be directed through the needle tip.

Preferably, the needles projects outward of the housing or, if the device has a protective displaceable cover, outward of the protective displaceable cover when the device is affixed to the subject by approximately 0.3 to 5.0 mm, more preferably 0.3–3.0 mm, most preferably 0.3–1.0 mm, and has an outer diameter of 0.075–0.5 mm, most preferably 0.1–0.2 mnm and an inner diameter of 0.05–0.3 mm, more preferably 0.05–0.15 mm, most preferably 0.05–0.075 mm. Such a needle is relatively painless to apply, causes little or no trauma to the skin and yet allows precisely controllable delivery of a liquid drug, including drugs of relatively large molecular size.

Preferably, the reservoir is in the form of an expansible-contractible chamber which is expanded when filled with the drug and which can be contracted to dispense the drug therefrom.

Further, preferably, the drug reservoir, when filled, has a volume of 0.2–10.0 ml or larger, more preferably 0.3–6.0 ml, most preferably 0.5 to 3.0 ml.

Further, preferably, the means for actively discharging the drug comprises an electrically controlled gas generator within the housing for generating a gas to contract the drug reservoir in order to discharge the drug therefrom.

Such an intradermal delivery device provides precise control over the rate of delivery of the drug; in particular, it allows the drug to be delivered at precisely controllable slow rates. The use of a narrow needle is also advantageous for achieving slow rates of delivery, while still allowing the delivery of a variety of drugs, including those of relatively large molecular size.

Suitably, the gas generator is an electrolytic cell. In a preferred embodiment of the invention, the device further comprises a start button which is depressible in order to activate the means for actively discharging the drug from the drug reservoir, such as a start button which energizes a gas generator. Thus, the device may be supplied and stored for an indefinite period of time and yet be immediately activated when required.

Suitably, the device comprises an electronic circuit for controlling the time and rate of gas generation, thereby controlling the discharge of the drug from the drug reservoir. Preferably, the electronic circuit comprises a microprocessor which is programmable with respect to the time and rate of gas generation. For instance, the microprocessor can be programmed to deliver the liquid drug in a continuous infusion (constant or variable rate), in a pulsatile manner or in intermittent doses as well as in response to input from the subject, such as patient controlled analgesia.

It is thus possible to choose or devise a dosage regime which will suit the requirement both of the individual patient and of the drug to be delivered. For example, the device may comprise a microprocessor which controls the delivery such that the rate of delivery is varied during a 24 hour cycle as is necessary due to the differing requirements of drug dosage during period of activity, inactivity and sleep, and taking account of the subject's requirements in relation to food intake.

Alternatively, the subject might be provided with separate daytime and nighttime devices, each having a different electronic circuit for controlling the time and rate of drug delivery.

It may be desirable to automatically deliver certain drugs only when required by the subject, either by patient activation or passively, such as by a feedback mechanism. In such a case, there is provided a device wherein the housing further includes a sensor (feedback) for detecting a condition in the body of the subject and for controlling the delivery of the drug in response thereto. The sensor may be, for example, a temperature sensor, a pulse rate sensor, a blood glucose sensor, a blood pressure sensor or a pH sensor.

Thus, where a device is intended to deliver a fever-reducing drug, for example, it might be provided with a temperature sensor such that a detected increase in body temperature above a certain value would activate the drug delivery or increase the rate of drug delivery.

The sensor may rest against the skin, may be inserted through the skin, or may be within the device and separate from the skin.

According to one embodiment of the invention, the housing includes a plurality of drug reservoirs, each reservoir being contractible by a separate gas generator and communicating with an outlet cavity with which the single hollow needle also communicates. In one such embodiment, all of the drug reservoirs communicate in series with the outlet cavity. In an alternative embodiment, all of the drug reservoirs communicate in parallel with the outlet cavity.

Including a plurality of drug reservoirs provides for considerable variations in the amounts of drug which can be delivered, in the rates at which drug can be delivered and in the number of drugs which can be delivered by the same device. The provision of a plurality of reservoirs allows the device to be used in a range of situations for which a single reservoir device would be unsuitable.

A preferred embodiment of a device which is to deliver more than one drug has a housing which includes a plurality of drug reservoirs, each having a single hollow needle associated therewith. Such a device is especially suitable when the drugs are not suitable to mix with one another or when they are to be delivered separately or sequentially. Additionally, a secondary drug which is capable of reducing local irritation or pain caused by the hollow needle and/or the interaction of the primary drug with the skin of the subject can be either co-administered with the primary drug from the instant intradermal device or incorporated into the adhesive such that the secondary drug is passively transdermally administered when the device is affixed to the skin of the subject.

In an alternative embodiment of a device according to the invention wherein the reservoir is in the form of an expansible-contractible chamber, the means for actively discharging the drug comprises a spring which is stressed by the expansion of the drug reservoir upon filling it with a drug, and which tends to return to its unstressed condition to contract the reservoir and, thereby, to discharge the drug via the hollow needle.

In another alternative embodiment wherein the reservoir is in the form of an expansible-contractible chamber, the means for actively discharging the drug comprises a membrane which is stressed by the expansion of the drug reservoir upon filling it with a drug, and which tends to return to its unstressed condition to contract the reservoir and, thereby, to discharge the drug via the hollow needle.

Either of the last mentioned alternative embodiments provide for devices which can be reusable when provided with means for refilling the drug reservoir. This refilling may take place either upon removal of the device or in situ.

In another alternative embodiment of the device according to the invention, the means for actively discharging the drug comprises a deformable liquid-impermeable membrane and a rigid liquid-permeable membrane; one side of the deformable liquid-impermeable membrane defining one side of the drug reservoir; the opposite side of the deformable liquid-permeable membrane and one side of the rigid liquid-permeable membrane defining a saline reservoir for receiving a saline solution; the opposite side of the rigid liquid-permeable membrane defining, with a rigid part of the housing, a pure water reservoir for receiving pure water to expand the saline reservoir by osmosis, thereby to contact the drug reservoir in order to dispense the drug therefrom via the hollow needle.

Such a device provides for a predictable and continuous delivery of the liquid drug, whose rate of delivery can be chosen according to the volume, concentration and nature of the saline solution used, since the expansion of the saline reservoir (and thus the contraction of the drug reservoir) depends on the osmotic pressure across the membrane separating the pure water reservoir from the saline reservoir.

Preferably, the device further comprises a membrane which is permeable to the liquid drug and impermeable to solid impurities, the membrane covering the inner end of the hollow needle. The advantage of the membrane covering the inner end of the hollow needle is to filter out solid particles to prevent clogging of the needle. Preferably, the pore size of this membrane may range from 0.2 $\mu$m to 1.0 $\mu$m. Alternatively, particularly when the drug to be administered is a protein or peptide, the interior surface of the drug reservoir and/or hollow needle can be coated with a substance, such as a silicone coating, to minimize precipitation of the drug and/or reduce interactions (such as absorption) of the drug reservoir or needle with the administered drug.

The protective displaceable cover can be extendibly and retractably engaged in the cover mounting means. For instance, when the device is not in use, the cover edges or tabs extending from the cover can engage a first set of notches or cavities located in the cover mounting means such that the cover is positioned substantially parallel to the lower surface (surface that is closest to the subject's skin when in use) of the housing but distal from the lower surface of the housing so that the needle extends no further than the upper surface (surface that is furthest from the subject's skin when in use) of the cover. Thus, when the device is not in use, the needle is generally intermediate to and enclosed by the housing and the cover. As the device is pressed to the skin of the subject, the protective displaceable cover is disengaged from the first set of notches or cavities and moved so as to engage a second set of notches or cavities located in the cover mounting means to position the cover substantially parallel to the lower surface of the housing and proximal to the lower surface of the housing. In this snap-action manner, the displaceable cover moves close to the housing to allow the fixed hollow needle to extend through or past the cover mounting means and penetrate through the epidermis and into the dermis of the subject. Alternatively, the notches or cavities can be located in the protective displaceable cover and the edges or tabs located in the cover mounting means.

An adhesive or other means for affixing the lower surface of the cover in contact with the subject's skin holds the device in place during administration of the drug. As the device is removed from the subject, the needle is extracted from the skin and, due to the adhesive force of the adhesive, the protective displaceable cover moves or snaps back to the first set of notches or cavities. Thus, the needle, which again extends no further than the upper surface of the cover, is generally intermediate to and enclosed by the housing and the cover.

The number of notches or cavities in the first and second sets (and the corresponding tabs) can range from two to four or more notches or cavities, such as notches positioned on opposite sides of the housing, to a continuous notch or cavity circumventing the housing. Three notches or cavities spaced around a circular housing is a particularly advantageous configuration. The protective displaceable cover can cover substantially all of the lower surface of the housing or an area of the lower surface of the housing immediately surrounding the single hollow needle.

Alternatively, the cover mounting means can comprise screw means located in the housing which mate with screw means associated with the protective displaceable cover. Thus, the protective displaceable cover can be movably positioned with respect to the housing by screwing the protective displaceable cover onto the lower surface of the housing either before, during or after the device is affixed to the skin of the subject. This alternative embodiment has the advantage of maintaining a parallel alignment between the cover mounting means and the protective displaceable cover, thus preventing unnecessary sideways forces on the hollow needle.

Other means to movably attach the protective displaceable cover to the cover mounting means can be employed, such as interlocking steps or mated slides with stops (in the cover and the cover mounting means) in which the cover and cover mounting means are held in juxtaposition by, for instance, springs.

Additionally, the displaceable protective cover can be extendibly and retractably engaged in the cover mounting means so as to be capable of being positioned at a multiplicity of depths relative to the housing to allow the needle to project outwards from the cover to a multiplicity of different lengths. For instance, the displaceable protective cover can engage a third set of notches or cavities located intermediate to the first and second set of notches or cavities in the cover mounting means. In this manner, the depth of penetration of the needle into the skin of the subject when the device is in contact with the subject's skin can be easily varied to accommodate administration of the device to different parts of the body of the subject or to different thicknesses of skin.

The tip of the outer end of the single hollow needle can be cut at a bias, cut flat, made conical or made inverse conical to enhance the penetration of the drug into the skin of the subject. Furthermore, the outer end of the needle, whether cut at a bias, made conical, made inverse conical or cut flat, may be closed at the outer end; in this case, an opening in the hollow needle exists within, for example, 2.0 mm of the tip of the outer end of the single hollow needle to provide for delivery of the drug from the reservoir to the subject's skin via the needle. The inner end of the hollow needle may extend into the drug reservoir, may be flush with the bottom surface of reservoir, may comprise a fluted funnel shape, or otherwise be shaped to promote fluid flow of the drug from the reservoir through the needle.

The present invention also encompasses a method of delivering a biologically effective amount of a liquid drug intradermally to an animal subject, especially a human, comprising the steps of: (1) affixing an intradermal drug delivery device as described above to the skin of the subject, the drug delivery device having a lower surface for application to the skin of the subject; means for affixing the device in position with the lower surface in contact with the subject's skin; a drug reservoir within the device and containing a biologically effective amount of at least one one liquid drug; a single fixed hollow needle associated with the drug reservoir having an outer diameter of 0.5 mm or less, preferably 0.2 mm or less and extending through the lower surface and having an inner end communicating with the drug reservoir and an outer end projecting outwards a sufficient distance so as to penetrate through the epidermis and into the dermis when the device is affixed to the skin; and means for actively discharging at least one drug from the reservoir to the subject's skin via the needle; and (2) activating the means for actively discharging at least one drug to deliver a biologically effective amount of at least one drug to the subject.

As used herein, the term, "liquid drug", is meant to encompass any drug-containing fluid capable of being passed through the hollow needle in a controlled manner, such as a liquid, solution, gel or fine suspension. There is essentially no limitation on the type of liquid drug which can be used with the invention other than to exclude those liquid drugs which would be inappropriate to deliver to the subject intradermally or subcutaneously. Representative drugs include peptides or proteins, hormones analgesics, anti-migraine agents, anti-coagulant agents, anti-emetic agents, cardiovascular agents, anti-hypertensive agents, narcotic antagonists, chelating agents, anti-anginal agents, chemotherapy agents, sedatives, anti-neoplastics, prostaglandins and antidiuretic agents.

Typical drugs include peptides, proteins or hormones such as insulin, calcitonin, calcitonin gene regulating protein, atrial natriuretic protein colony stimulating factor, betaseron, erythropoietin (EPO), interferons such as $\alpha$, $\beta$ or $\gamma$ interferon, somatropin, somatotropin, somatostatin, insulin-like growth factor (somatomedins), luteinizing hormone release hormone (LHRH), tissue plasminogen activator (TPA), growth hormone releasing hormone (GHRH), oxytocin, estradiol, growth hormones, leuprolide acetate, factor VIII, interleukins such as interleukin-2, and analogues thereof; analgesics such as fentanyl, sufentanil, butorphanol, buprenorphine, levorphanol, morphine, hydromorphone, hydrocodone, oxymorphone, methodone, lidocaine, bupivacaine, diclofenac, naproxen, paverin, and analogues thereof; anti-migraine agents such as sumatriptan, ergot alkaloids, and analogues thereof; anti-coagulant agents such as heparin, hirudin, and analogues thereof; anti-emetic agents such as scopolamine, ondanesetron, domperidone, metoclopramide, and analogues thereof; cardiovascular agents, anti-hypertensive agents and vasodilators such as diltiazem, clonidine, nifedipine, verapamil, isosorbide-5-mononitrate, organic nitrates, agents used in the treatment of heart disorders, and analogues thereof; sedatives such as benzodiazepines, phenothiozines, and analogues thereof; narcotic antagonists such as naltrexone, naloxone, and analogues thereof; chelating agents such as deferoxamine, and analogues thereof; anti-diuretic agents such as desmopressin, vasopressin, and analogues thereof; anti-anginal agents such as nitroglycerine, and analogues thereof; anti-neoplastics such as 5-fluorouracil, bleomycin, and analogues thereof; prostaglandins and analogues thereof; and chemotherapy agents such as vincristine, and analogues thereof.

Figure 2:
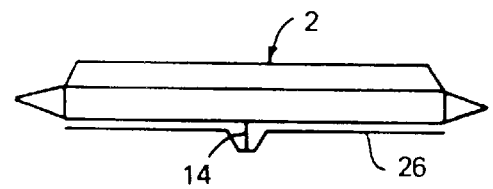
FIG. 2 is a side elevational view of the device of FIG. 1.
Figure 3:
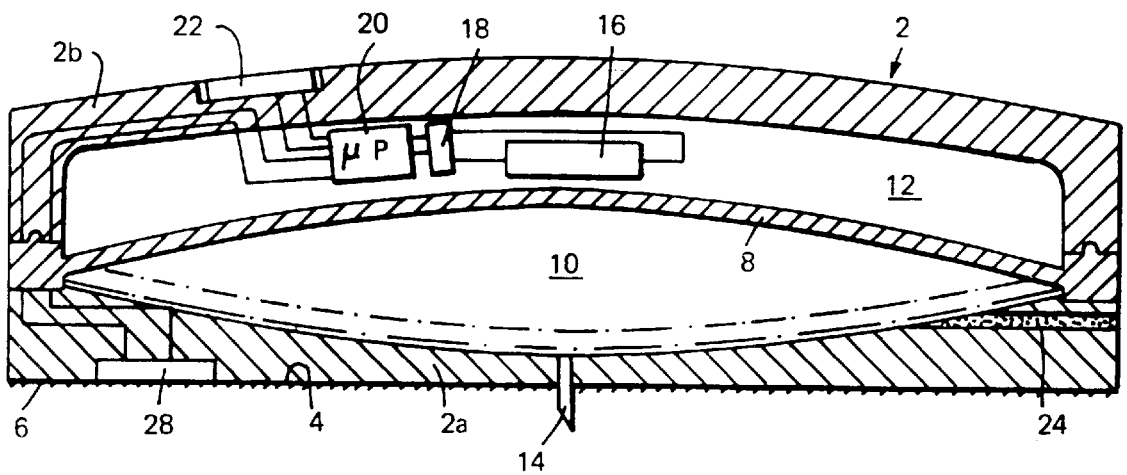
FIG. 3 is an enlarged longitudinal sectional view of the device of FIG. 1.

The Embodiment of FIGS. 1–3

The intradermal drug delivery device illustrated in FIGS. 1–3 includes a housing 2 of disc or cylindrical configuration having a flat lower surface 4 coated with a pressure-sensitive adhesive 6 for adhering the housing to the skin of the subject to receive the drug. The interior of housing 2 includes a flexible liquid-impermeable membrane 8 defining an expansible-contractible chamber 10 between it and the lower section 2a of hosing 2, and a second expansible-contractible chamber 12 between it and the upper section 2b of the housing. Chamber 10 serves as a reservoir for receiving the drug to be delivered, whereas chamber 12 serves as a gas chamber for controlling the delivery of the drug from the reservoir 10.

A hollow needle 14 extends through the housing section 2a. The inner end of needle 14 communicates with the drug reservoir 10, whereas the outer end of the needle projects outwardly of the flat surface 4 of the housing a short distance so as to penetrate the epidermis of the subject's skin when the housing is applied and adhered thereto. Preferably, hollow needle 14 projects outwardly of the flat surface 4 a distance of 0.3–1.0 mm, just sufficient to penetrate through the epidermis of the subject's skin. The outer diameter of the needle is preferably from 0.1–0.2 mm and its inner diameter is preferably from 0.05.–0.075 mm. These dimensions permit a slow, precisely-controllable delivery of drug from the drug reservoir 10. The inner end of the hollow needle 14 may be covered by a filter membrane to prevent clogging particles from entering the needle.

The rate and time of delivery of the drug is controlled by a gas-generator 16 within the gas compartment 12. Preferably, gas generator 16 is an electrolytic cell energized by a battery 18 and controlled by a microprocessor 20 when actuated by a START button 22 mounted on housing section 2b.

Housing section 2a further includes an injection plug 24 which may be pierced by a syringe needle, for example, in order to fill reservoir 10 with the drug to be dispensed. In addition, the adhesive coating 6 on the flat lower surface 4 of the housing section 2a is normally covered by a protective strip 26 (FIG. 2) which is peeled away when the device is to be used. Protective strip 26 preferably includes a tab extension 27 (FIG. 1) to facilitate removing the strip.

Optionally, housing section 2a further includes a sensor 28 flush with surface 4 so as to be pressed against the skin of the subject when the device is applied to the subject and held by the adhesive coating 6. For instance, sensor 28 may be a temperature sensor for sensing the temperature of the subject and for controlling microprocessor 20, and thereby the dispensing of the drug, in response to the subject's temperature. Sensor 28 may be a pulse rate sensor for sensing the pulse rate of a subject and for controlling, via processor 20, the dispensing of the drug in response thereto.

It will be seen that the device illustrated in FIGS. 1–3 may be used in the following manner.

Drug compartment 10 is filled with the drug to be dispensed by injecting same via a syringe needle through the injection plug 24, thereby expanding the drug reservoir 10, e.g., to the full-line position shown in FIG. 3. Microprocessor 20 is preprogrammed according to the desired time and rate of delivery of the drug. Protective strip 26 is removed to expose the hollow needle 14, and the device is then pressed against the subject's skin such that the needle 14 penetrates only through the epidermis. The adhesive coating 6 firmly adheres the device to the subject's skin.

When the delivery is to start, the START button 22 is depressed. This energizes the electrolytic cell 16 to generate a gas under the control of microprocessor 20. This increases the pressure within gas chamber 12, thereby deforming membrane 8 to contract the drug chamber 10, to feed the drug from chamber 10 to the subject via the hollow needle 14 at a rate dependent on the rate of generation of the gas by the gas generator 16. This rate is controlled by the microprocessor 20.

The sensor 28 senses a predetermined condition of the subject and controls the delivery of the drug from reservoir 10 in accordance therewith. For example, sensor 28 may be a temperature sensor, for controlling the delivery of a fever-reducing drug; alternatively, it could be a pulse rate sensor or a blood pressure sensor for controlling the delivery of a drug appropriate to the sensed condition.

Figure 4:
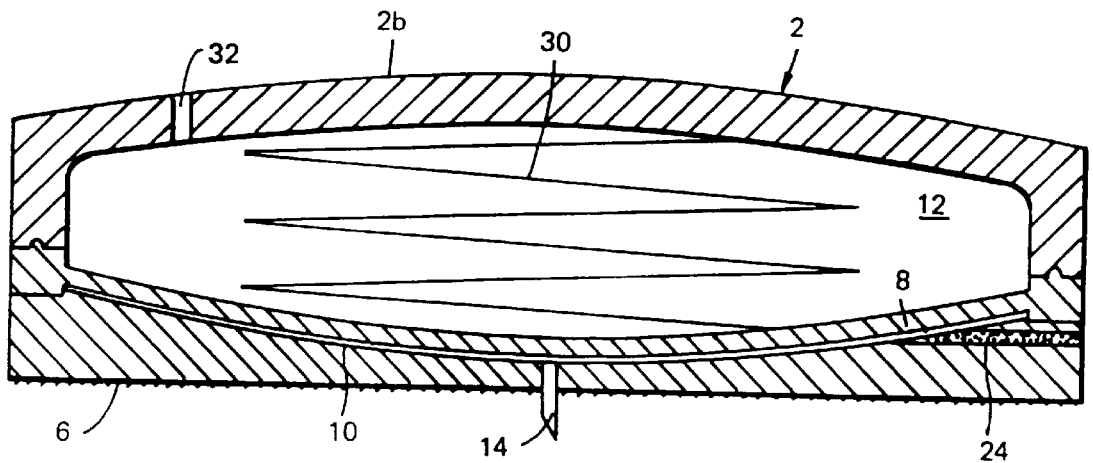
FIG. 4, 5 and 6 are longitudinal sectional view illustrating other intradermal drug delivery devices constructed in accordance with the invention.

The Embodiment of FIG. 4

FIG. 4 illustrates a similar device to that illustrated in FIGS. 1–3, and therefore corresponding parts have been identified by the same reference numbers. In the construction illustrated in FIG. 4, however, the drug reservoir 10 is contracted to feed the drug via the hollow needle 14, not by a gas generator as in FIGS. 1–3, but rather by a spring 30 included in compartment 12 between the diaphragm 8 and the housing section 2b. The latter section is formed with an atmospheric vent 32.

The device illustrated in FIG. 4 is used in the same manner as described above with respect to FIGS. 1–3, except that, instead of effecting the delivery of the drug by means of a gas generator under the control of a microprocessor as in FIGS. 1–3, the delivery of the drug is effected by spring 30 which is pre-stressed upon introducing the drug into reservoir 10 via the injection plug 24.

Figure 5:
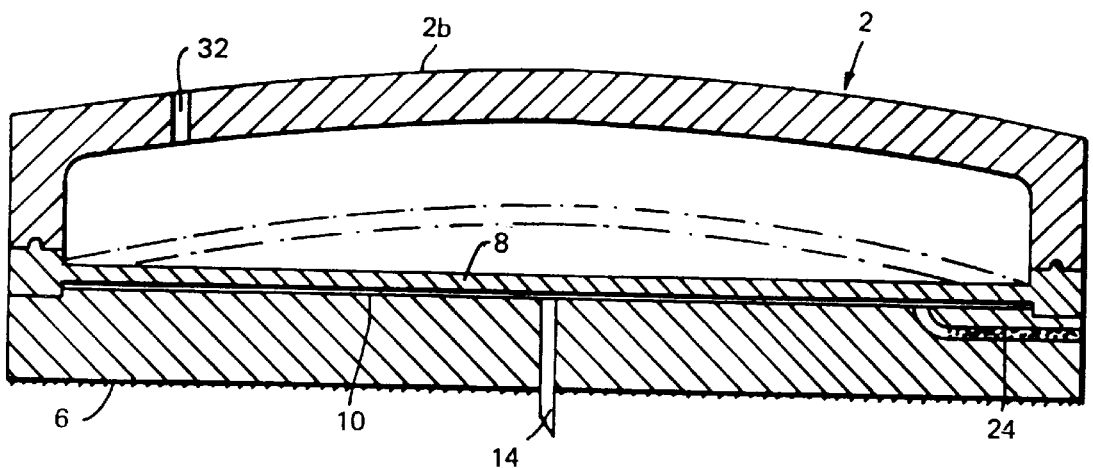

The Embodiment of FIG. 5

The device illustrated in FIG. 5 is similar to that illustrated in FIG. 4, and therefore its corresponding parts are identified by the same reference numbers. In the device of FIG. 5, however, instead of including a spring (30) which is stressed upon filling the chamber 10 with the drug, the diaphragm 8 is made of an elastic material which is pre-stressed when so filling the drug chamber, and thereby effects the delivery of the drug via the hollow needle 14.

Figure 6:
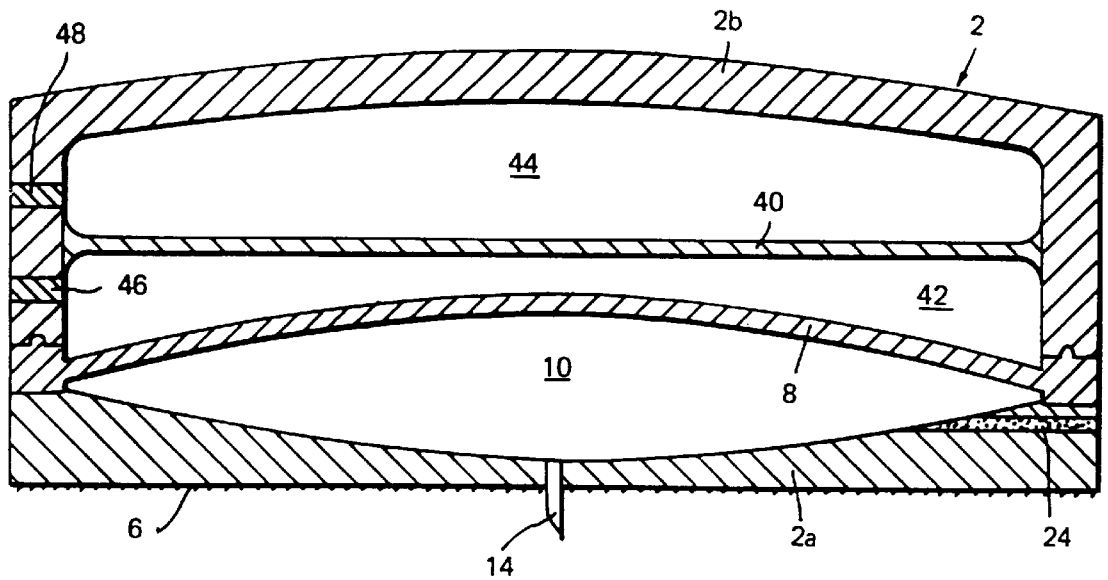

The Embodiment of FIG. 6

FIG. 6 illustrates another device similar to those described earlier, and therefore the corresponding parts are also identified by the same reference numerals. In this case, however, the housing 2 includes not only the deformable liquid-impermeable membrane 8, but also a rigid liquid-permeable membrane 40. Thus, one side of the impermeable membrane 8 defines with housing section 2a the drug reservoir 10, whereas the other side of membrane 8 defines, with one side of the rigid liquid permeable membrane 40, a saline chamber 42. The other side of the permeable membrane 40 defines with housing section 2b a pure water chamber 44. Drug reservoir 10 may be filled as described above via the injection plug 24. The saline chamber 42 may be filled via another injection plug 46, and the pure water chamber 44 may be filled via another injection plug 48.

It will be seen that when the three chambers 10, 42 and 44 are filled as described above, water from chamber 44 will permeate by osmosis through membrane 40 into the saline chamber 42, thereby expanding the chamber and contracting the drug reservoir 10, forcing the drug out through the hollow needle 14.

Figure 7:
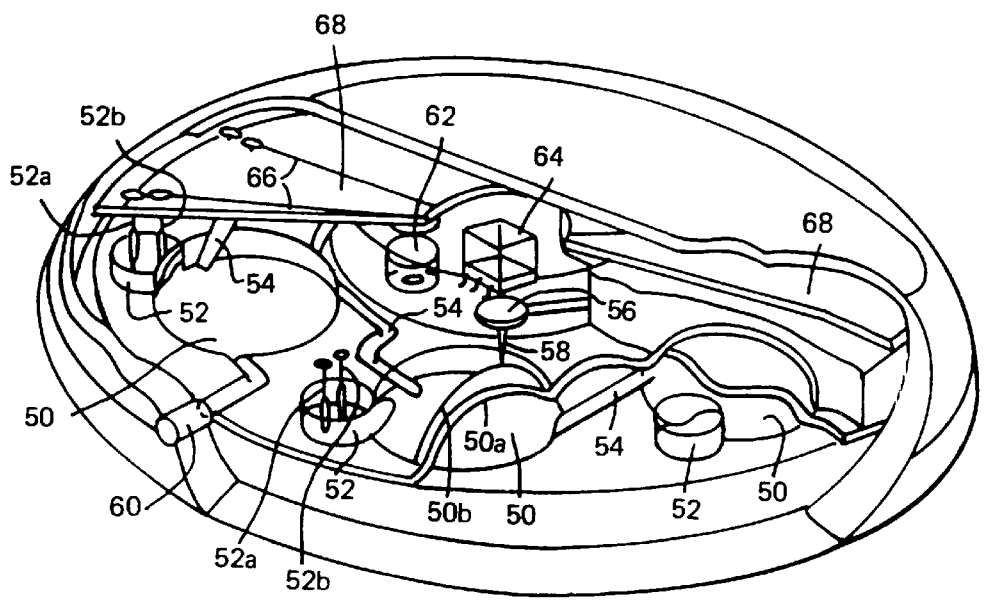
FIG. 7 is a diagrammatic view illustrating a multi-reservoir intradermal drug delivery device in accordance with the invention.
Figure 8:
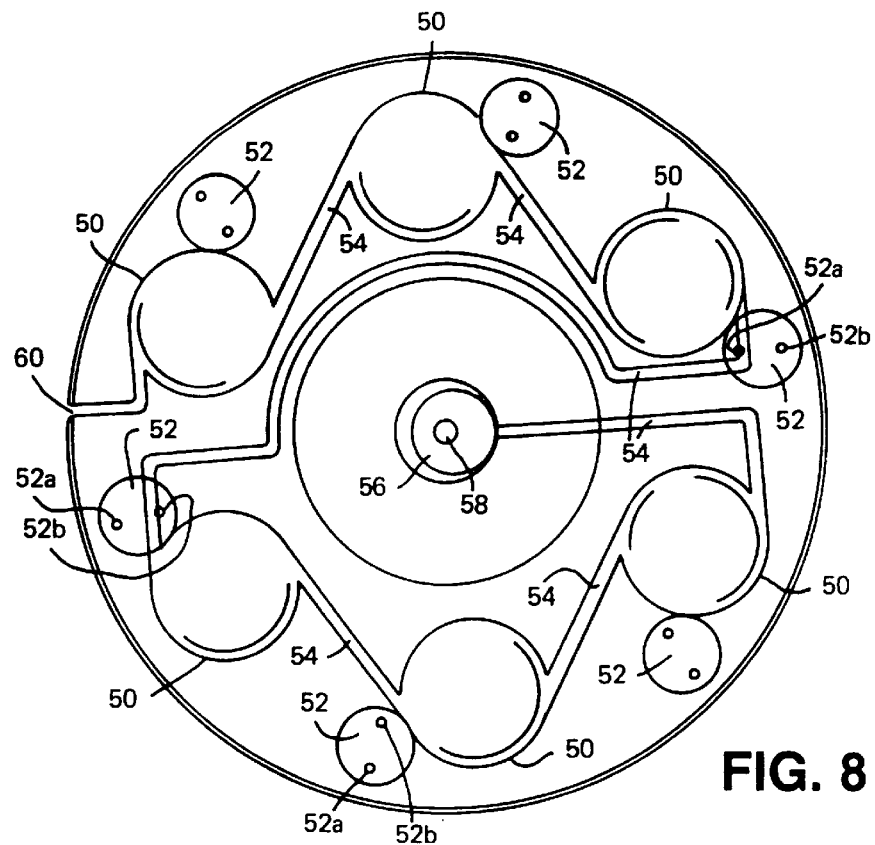
FIG. 8 is a top plan view more particularly illustrating the internal structure of the device of FIG. 7.

The Embodiment of FIGS. 7 and 8

FIGS. 7 and 8 illustrate a device similar to that illustrated in FIGS. 1–3, except that the device includes a plurality of separate drug reservoirs 50 (six being shown in FIG. 8 for example), each individually controlled by a gas generator 52. All the drug reservoirs are connected in series via conduits 54 to a central outlet cavity 56 with which the hollow needle 58 communicates. An injection plug 60 may be used for filling all the reservoirs 50 in series.

Each of the gas generators 52 is a separate electrolytic cell including a pair of electrodes 52a, 52b for applying electrical current to an electrolyte within the cell, thereby generating a gas within the cell corresponding to the electrical current applied. The so-generated gas is applied to the gas chamber of its respective drug reservoir 50, i.e. between a displaceable diaphragm 50a (FIG. 7) and a rigid cover 50b, to thereby contract the drug reservoir and to feed its drug via its conduit 54 to the outlet cavity 56, which is in communication with the injection needle 58.

The electrolytic cells 52 are energized by a battery 62 (FIG. 7) under the control of a microprocessor 64 via electrical conductors 66 carried by a printed circuit board 68 connected to the electrodes 52a, 52b of each electrolytic cell.

It will be seen that including a plurality of drug reservoirs 50 each separately controllable by its own gas generator 52, enables the device to be controlled to provide a wide range of dispensing rates. The series connections of the drug reservoirs with the outlet cavity 56, which is in communication with the injection needle 58 permits the device to be conveniently primed by injecting the drug via injection plug 60 into all the reservoir in series until the drug begins to discharge through the needle.

Figure 9:
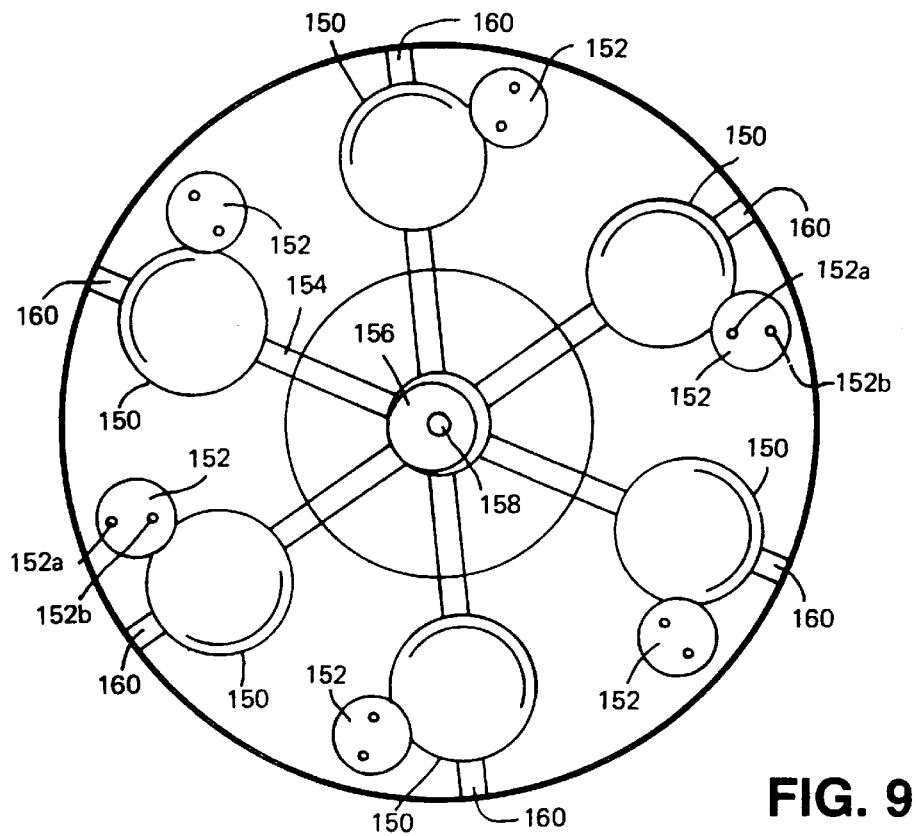
FIG. 9 is a view corresponding to that of FIG. 8, but showing a modification wherein the drug reservoirs are connected in parallel with the outlet cavity rather than in series as in FIG. 8.

The Embodiment of FIG. 9

FIG. 9 illustrates a variation in the construction of the device of FIGS. 7 and 8, in that the plurality of drug reservoirs, therein designated 150, are connected, via their respective conduits 154, to the outlet cavity 156, which is in communication with the injection needle 158. As in the device of FIGS. 7 and 8, the device of FIG. 9 is also provided with a separate gas generator 152, e.g., an electrolytic cell, for each of the plurality of drug reservoirs 150. Each reservoir is separately filled via its own injection plug 160.

It will be seen that the device illustrated in FIG. 9 permits the delivery of a single drug, or a mixture of drugs, all under the control of the microprocessor (e.g., 64, FIG. 7). Thus, if a large quantity of drug is to be delivered, the microprocessor could be preprogrammed to energize a plurality of the electrolytic cells 152 at one time; and if two or more drugs are to be simultaneously delivered, the various reservoir 150 would be filled with the respective drugs and dispensed as required under the control of the microprocessor.

Figure 10:
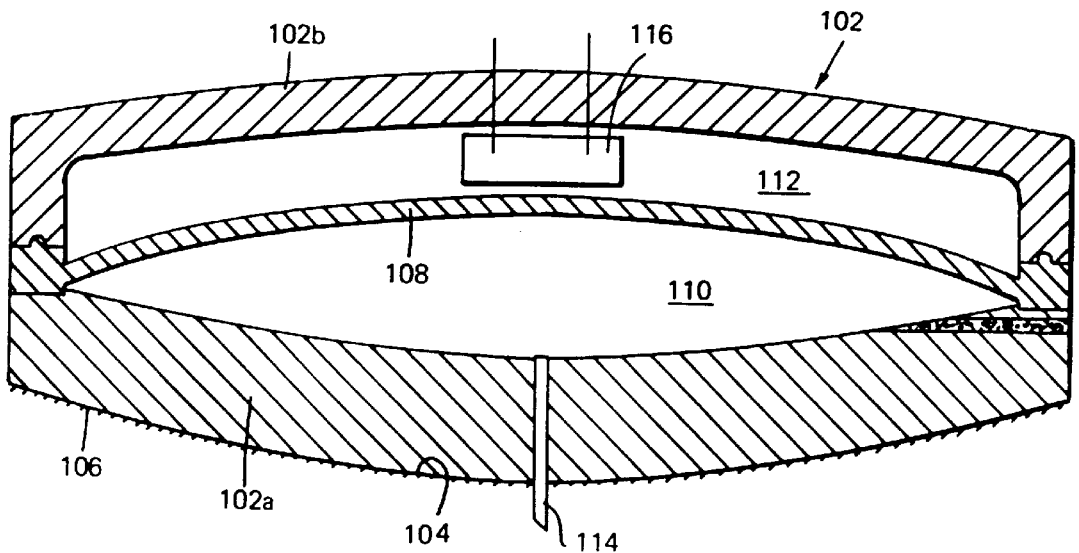
FIGS. 10 and 11 illustrate two further variations in the construction of the device.
Figure 11:
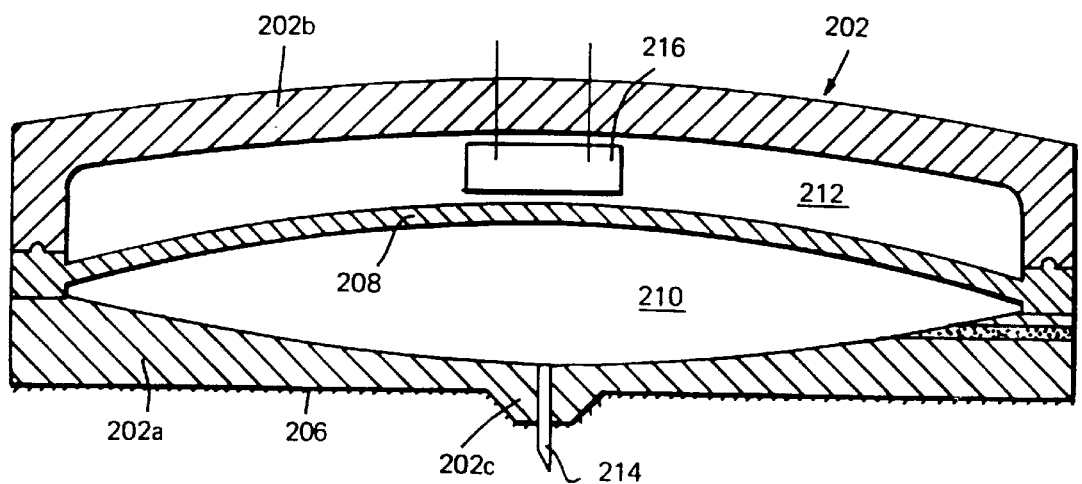
Figure 12:
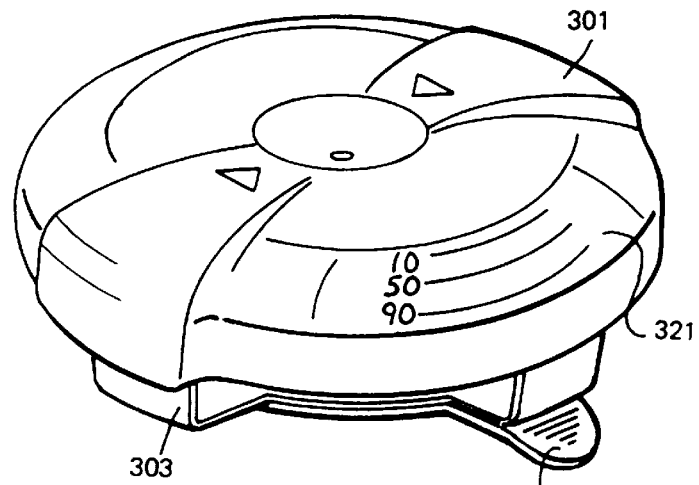
FIG. 12 illustrates a form of the intradermal drug delivery device having a protective displaceable cover constructed in accordance with the present invention.
Figure 13:
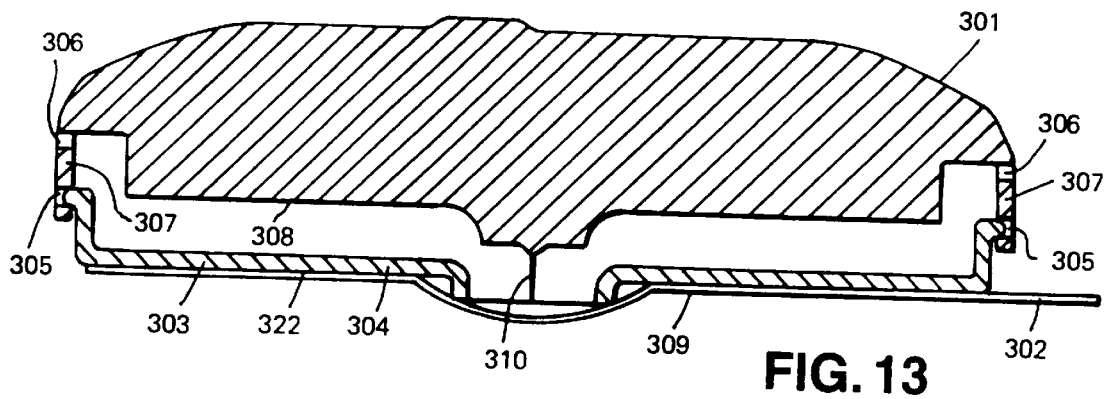
FIGS. 13 and 14 are side elevational views of the device of FIG. 12 in which the protective displaceable cover is extended and retracted, respectively.
Figure 14:
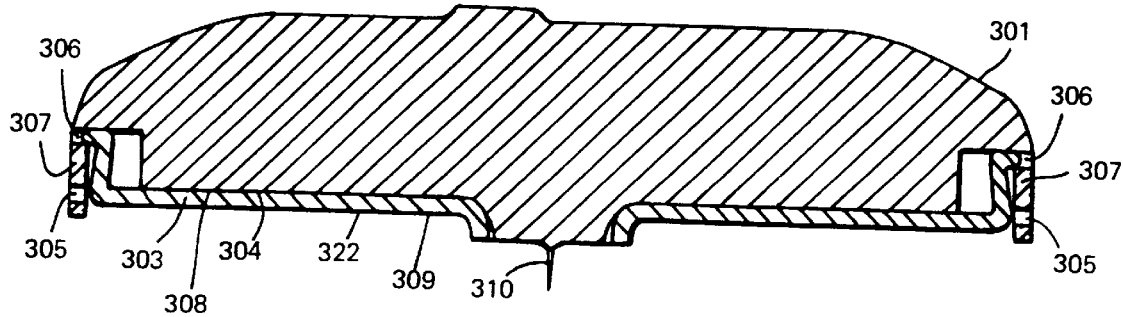

The Embodiments of FIGS. 10 and 11

While the above-described embodiments, the lower surface of the housing (e.g., 4) is flat, FIGS. 10 and 11 illustrate variations in this construction. Thus, FIG. 10 illustrates the housing 102 having a housing section 102a of convex configuration on the lower surface 104 and coated with the pressure-sensitive adhesive 106. A diaphragm 108 divides the interior of the housing into a drug reservoir 110 and a gas chamber 112 containing an electrolytic cell gas generator 116. The hollow needle 114 extends through the center of the lower surface 104 of the housing, and is dimensioned as described above to penetrate through the epidermis of the subject's skin. FIG. 11 illustrates a similar construction, except that the housing section 202a of the housing 202 is formed with a central projection 202c through which the hollow needle 214 extends.

The constructions of FIGS. 10 and 11 counteract the natural resilience or stretching of the skin when the device is applied, so as to achieve penetration of the epidermis by the needle. The use of a narrow diameter hollow needle minimizes trauma, minimizes leakage and better ensures more controlled delivery.

The Embodiment of FIGS. 12–15 and FIG. 21

The embodiments illustrated in FIGS. 1–11 are designed to operate without a protective displaceable cover. The present invention also provides for embodiments having a protective displaceable cover. For instance, the intradermal drug delivery device illustrated in FIGS. 12–15 and FIG. 21 includes housing 301 (301a and 301b in FIG. 15 and FIG. 21) of approximately disc or cylindrical configuration and having a lower surface 308. Other convenient housing shapes, such as rectangular, hexagonal, ovoid, etc. are also contemplated by the present invention. Protective displaceable cover 303 having an upper surface 304 and a lower surface 322 is attached to housing 301 via cover mounting means 307, which comprise a first set of notches or cavities 305 and a second set of notches or cavities 306. The lower surface 322 of the protective displaceable cover 303 is coated with a pressure-sensitive adhesive or doubled-sided adhesive 309 for affixing the cover 303 to the skin of the subject to receive the drug. Optional release line 302, which is peeled away prior to application of the device to the subject, projects the device prior to use.

The interior of housing 301 includes a flexible liquid-impermeable membrane 311 defining an expansible-contractible drug reservoir 312 between it and the lower section 301b of housing 301, and a second expansible-contractible electrolyte chamber 313 between it and the upper section 301a of housing 301. Chamber 312 serves as a reservoir for receiving the drug to be delivered, whereas chamber 313 serves as a gas chamber for controlling the delivery of the drug from the reservoir 312.

Hollow needle 310 extends through housing section 301b. The inner end of needle 310 communicates with the drug reservoir 312, whereas the outer end of the needle projects outwardly of the housing lower surface 308. When cover 303 is retracted (e.g., attached via notches or cavities 306), hollow needle 310 extends outwardly of the lower surface 322 of the protective displaceable cover 303 a short distance so as to penetrate through the epidermis and into the dermis when the cover 303 is affixed to the subject's skin. Preferably, hollow needle 310 projects outwardly of the cover 303 a distance of approximately 0.3–5.0 mm, more preferably 0.3–3.0 mm, most preferably 0.3–1.0 mm, and has an outer diameter of 0.075–0.5 mm, most preferably 0.1–0.2 mm and an inner diameter of 0.05–0.3 mm, more preferably 0.05–0.15 mm, most preferably 0.05–0.075 mm. These dimensions permit a slow, precisely-controllable delivery of the drug from the drug reservoir 312. The inner end of hollow needle 310 may be covered by a filter membrane 320 to prevent clogging from particles entering the needle. Optionally, the inner end of hollow needle 310 may extend into reservoir 312, may be flush with the bottom surface of reservoir 312, may comprise a fluted funnel shape, or otherwise be shaped to promote fluid flow of the drug from reservoir 312 through needle 310. The tip of the outer end of single hollow needle 310 can be cut at a bias, cut flat, made conical or made inverse conical or otherwise shaped to enhance the penetration of the drug into the skin of the subject. Furthermore, the outer end of needle 310, whether cut at a bias, made conical, made inverse conical or cut flat, may be closed at the outer end; in this case, an opening in the hollow needle exists within, for example, 2.0 mm of the tip of the outer end of the single hollow needle to provide for delivery of the drug from the reservoir to the subject's skin via the needle.

Optionally, diaphragm backing disc 314, e.g. a plastic disc, abuts diaphragm 311 to maintain a relatively parallel orientation between diaphragm 311 and lower housing 301b. Seal 315, e.g., a silicone elastomer, is multi-functional. For instance, seal elastomer 315 seals gaseous electrolyte chamber 313 from the outside environment, provides a housing for electrodes 316a and 316b, optionally comprises an injection port 315b for injection of the electrolyte into the electrolyte chamber 313, and optionally comprises occlusion switch diaphragm 315a, which upon occlusion in the path of drug delivery or after the deliverable amount of drug has been delivered elevates contact 317, which disconnects contact 317 from contact/electronic circuit 318 to terminate current supply from battery 319 to the electrolytic cell. Optional filter 320 prevents small particles from entering and clogging needle 310. The rate and time of delivery of the drug is controlled by the electrolytic cell energized by battery 319 when actuated by the on/off switch (not shown in FIGS. 12–15 and FIG. 21). Optionally, a microprocessor (not shown in FIGS. 12–15 and FIG. 21) can be included in the electronic circuit to further control the rate and time of delivery of the drug.

Figure 21:
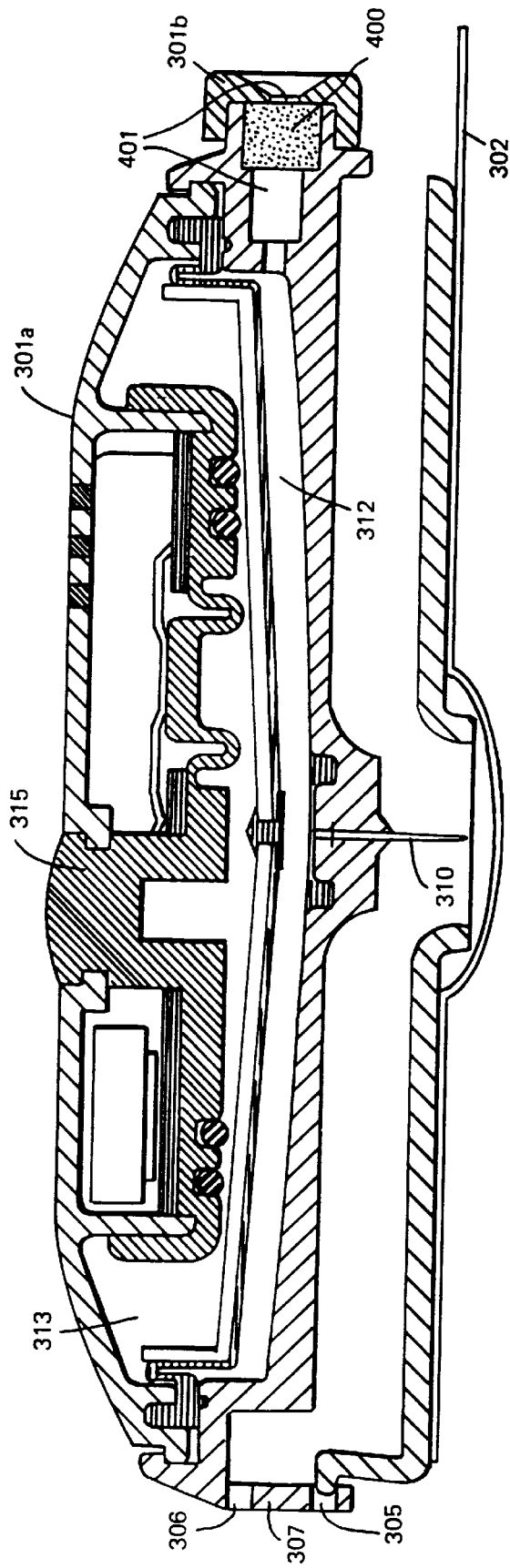
FIG. 21 shows an enlarged longitudinal sectional view of the drug delivery device of FIG. 12 illustrating a drug injection port.

Similar to FIG. 3, the at least one drug can be loaded into the device of FIGS. 12–15 via a syringe needle, which may sealably pierce housing 301 or via an injection port through housing 301. FIG. 21 illustrates one configuration for a drug injection port. In this configuration, three pairs of notches or cavities 306 and 305 are spaced substantially equidistant around the circumference of housing 301b. Opposite one pair of notches or cavities 306 and 305 is injection port 401, which is plugged by plug 400, e.g., an elastomer plug. Drug reservoir 312 is filled with the drug to be dispensed by injecting the drug via a syringe needle through plug 400 and injection port 401 into drug reservoir 312. For instance, to fill and prime the device, the device can be placed upside down so that needle 310 is directed upwards and the drug can be injected into drug reservoir 312 with air venting from needle 310. The convex shape of drug reservoir 312 promotes exhaustion of the air from the reservoir as drug is injected to prime the device.

It will be seen that the device illustrated in FIGS. 12–15 and FIG. 21 may be used in the following manner. Drug reservoir 312 is filled with the drug to be dispensed, thereby expanding the drug reservoir 312. Upon removal of the release liner 309, the device is pressed against the subject's skin. As pressure is applied to housing 301, the displaceable protective cover 303 moves by snap action from engagement in notches or cavities 305 to notches or cavities 306 such that needle 310 penetrates through the displaceable protective cover and through the subject's epidermis. The adhesive 309 firmly adheres the device to the subject's skin. Following actuation of the on/off switch, the electrolytic cell is energized and produces a gas which increases the pressure within electrolyte chamber 313, deforms membrane 311 to contract the drug chamber 312 and feeds the drug from reservoir 312 to the subject via the hollow needle 310.

Confirmation that the device is delivering/has delivered the at least one drug to the subject can be obtained by viewing the level of the electrolyte in electrolyte chamber through optional transparent window 321. The amount of drug that is delivered to the subject during a treatment period can be ascertained by visual observation, particularly if a dye is incorporated into the electrolyte. Upon termination of therapy, the device is removed from the subject. Application of force to remove the device from the subject's skin (to separate the adhesive 309 from the skin) results in the protective displaceable cover moving by snap action from engagement in notches or cavities 306 to notches or cavities 305.

Figure 17A:
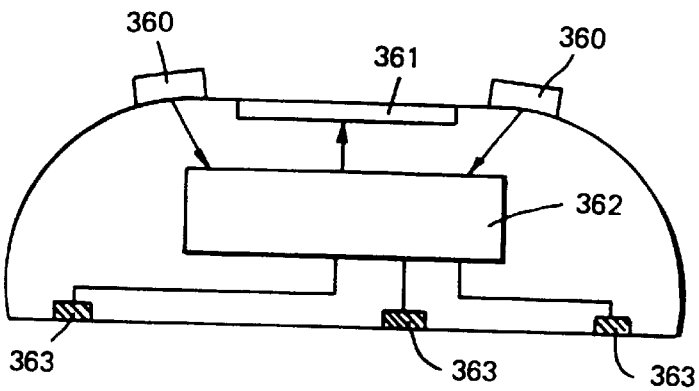
FIGS. 17(a)–(c) are longitudinal sectional views illustrating electronic control units of a two-part intradermal drug delivery device constructed in accordance with the present invention which provide for fully programmable delivery, patient activated delivery and continuous delivery, respectively.
Figure 17B:
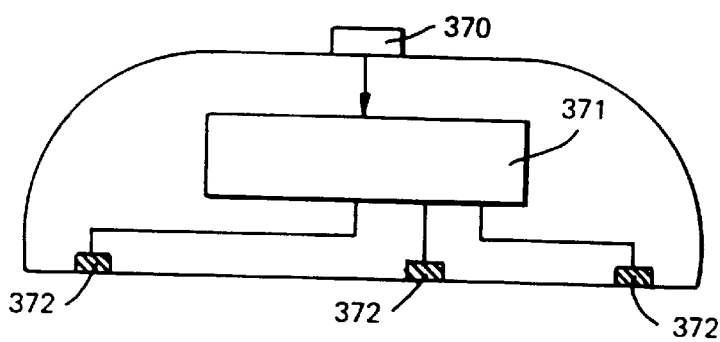
Figure 17C:
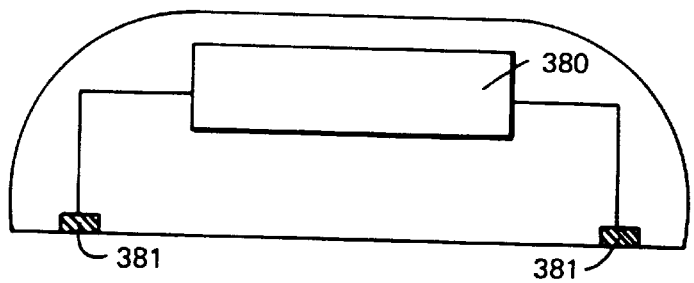
Figure 18:
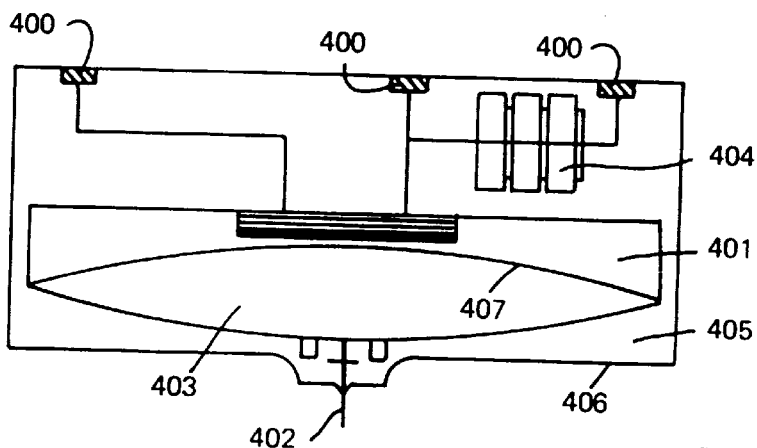
FIG. 18 is a longitudinal sectional view illustrating the disposable cartridge unit of a two-part intradermal drug delivery device constructed in accordance with the present invention.

Best Mode for Carrying Out the Invention
The Embodiments of FIGS. 16–18

The embodiments shown in FIGS. 1–15 are designed to be wholly disposable. The present invention also provides for two-part intradermal drug delivery devices in which the electronic control unit (see FIG. 17) can be reused while the disposable cartridge unit (see FIGS. 16 and 18) is disposable and replaceable. The combination of the units illustrated in FIG. 16 and FIG. 17 provides for a two-part device similar to the one-part embodiments illustrated in FIGS. 12–15 and FIG. 21 while the combination of the units illustrated in FIG. 17 and FIG. 18 provides for a two-part device similar to the one-part embodiments illustrated in FIGS. 1–11.

FIG. 17 illustrates three basic models for the reusable electronic control unit according to the present invention. FIG. 17(a) illustrates a fully programmable electronic control unit having microprocessor 362 in electrical communication with push buttons 360 and display 361, such as a liquid crystal display, as well as disposable cartridge contacts 363. This unit can be fully programmable with respect to the time and rate of gas generation and allows for delivery of the liquid drug at a variety of delivery protocols, including continuous infusion at a constant or variable rate, pulsatile or intermittent delivery and delivery in response to input from the subject, such as patient controlled analgesia. Similarly, FIG. 17(b) illustrates a patient controlled electronic control unit having microcontroller 371 in electrical communication with push button 370 and disposable cartridge contacts 372. This unit is particularly useful for use in patient controlled analgesia. Likewise, FIG. 17(c) illustrates an electronic control unit preprogrammed for continuous delivery having current controller 380 in electrical communication with disposable cartridge contacts 381. The choice of the particular electronic control unit determines the range of different electronic control features available when an electronic control unit is combined with a disposable cartridge. While on/off buttons can be incorporated in the electronic control units, activation of the two-part embodiments formed from the combination of the units illustrated in FIGS. 16–18 is automatically accomplished by engaging a particular electronic control unit with a disposable cartridge unit (engaging means not shown) so that contacts 350 or 400 are in electrical communication with contacts 363, 372 or 381.

FIG. 16 illustrates a disposable cartridge unit according to the present invention which incorporates all of the features found in the embodiments illustrated in FIGS. 12–15 and FIG. 21 (including the presence of a protective displaceable cover) except that (1) contacts/electronic circuit of FIG. 15 are replaced by contacts 351 of FIG. 16, (2) an on/off switch is not present in the disposable cartridge unit of FIG. 16 and (3), the disposable cartridge of FIG. 16 possesses multiple electronic control unit contacts 350 which are capable of electrically contacting disposable cartridge contacts 363, 372 or 381 of the electronic control units illustrated in FIG. 17(a), (b) and (c), respectively, when the two units are engaged.

Similarly, the disposable cartridge unit of FIG. 18 is similar to the one-part devices shown in FIGS. 1–11. For instance, the disposable cartridge unit of FIG. 18 includes a housing 405 having a lower surface 406 coated with a pressure-sensitive or double-sided adhesive for adhering the housing to the skin of the subject to receive the drug. The interior of housing 405 includes a flexible liquid-impermeable membrane 407 defining an expansible-contractible drug reservoir chamber 403 between it and the lower section of housing 405, and a second expansible-contractible electrolyte chamber 401 between it and the upper section of housing 405. Chamber 403 serves as a reservoir for receiving the drug to be delivered, whereas chamber 401 serves as a gas chamber for controlling the delivery of the drug from the reservoir 403. Hollow needle 402 of FIG. 18 corresponds to battery 18 of FIGS. 1–3. Similar to FIG. 16, electronic control unit contacts 400 are capable of electrically contacting the disposable cartridge contacts 363, 372 or 381 of the electronic control units illustrated in FIG. 17(a), (b) and (c), respectively, when the two units are engaged.

EXAMPLE 1

Figure 19:
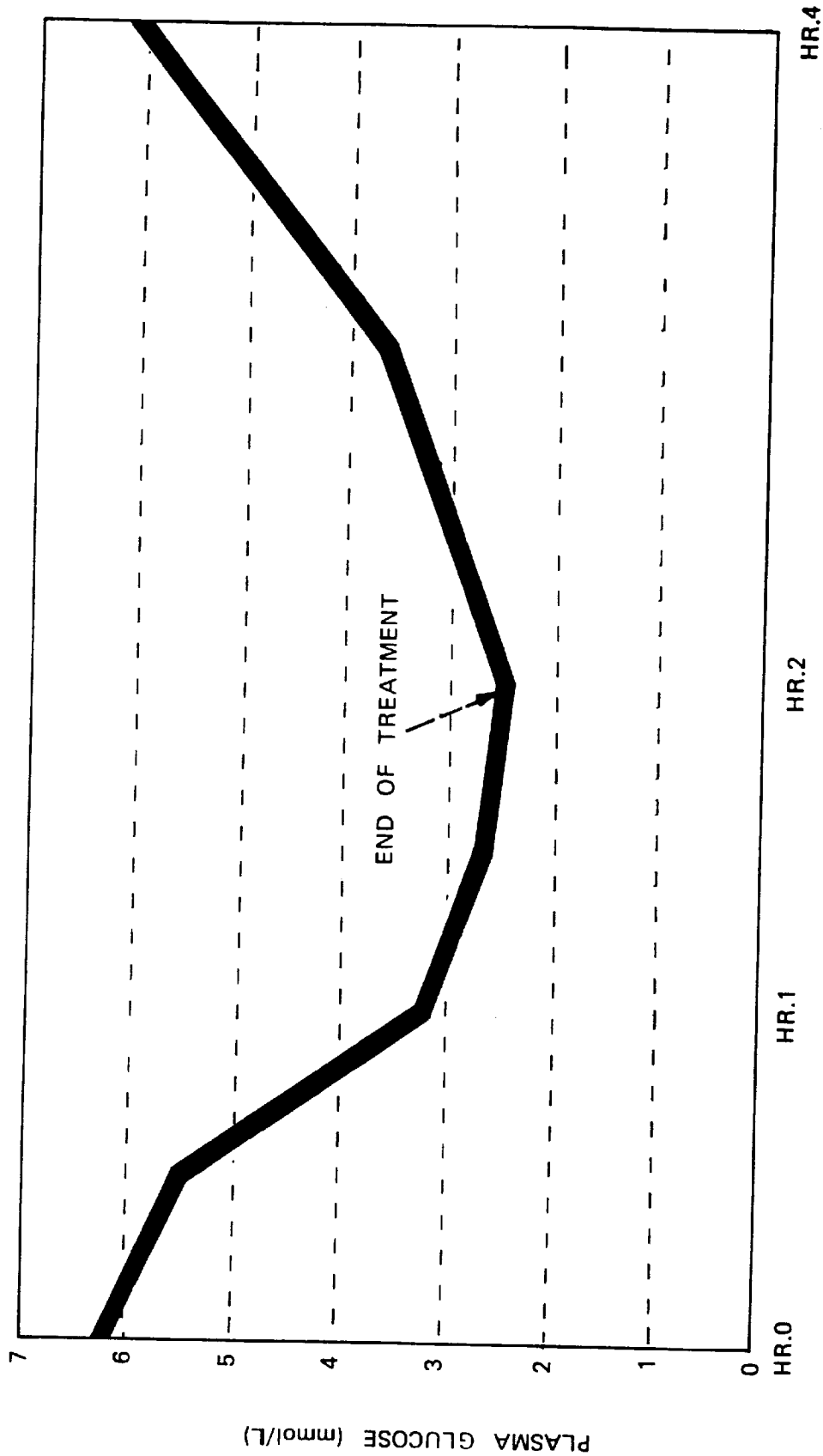
FIGS. 19 and 20 show delivery characteristics of insulin and salmon calcitonin, respectively, from a device constructed in accordance with the invention.

A device according to the present invention containing 0.6 ml of a solution of insulin (100 I.U./ml) was affixed to each of two rabbits and the devices were switched on. The insulin solution was infused at a rate of 0.1 ml/hour for two hours. As shown in FIG. 19, blood glucose concentrations for these rabbits were measured at various times following activation of the devices. At one hour, mean blood glucose concentration had fallen from a control value of 6.25 mmol/l to 3.2 mmol/l. This value stayed relatively constant at 1.5 hours following activation (2.65 mmol/l) and at 2 hours (2.5 mmol/l), at which time the devices were removed. One hour later the mean value was 3.7 mmol/l, which value continued to rise with time.

EXAMPLE 2

Figure 20:
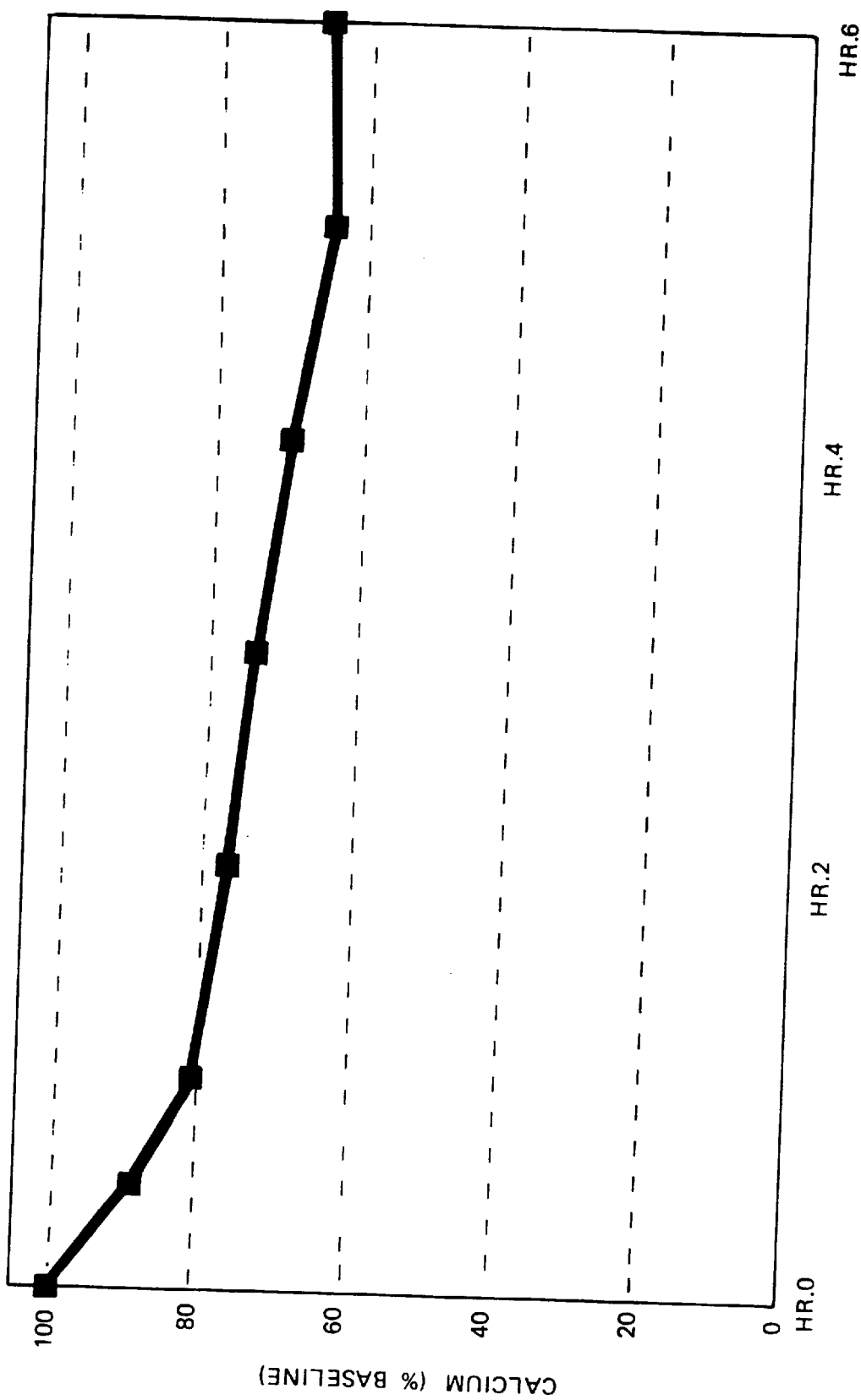

A device according to the present invention containing 0.6 ml of a solution of salmon calcitonin (1.0 mg/ml) was affixed to each of four rabbits. This solution was infused at the rate of 0.1 ml/hour for 6 hours. Serum calcium concentrations were measured via an ear vein at 0, 0.5, 1, 2, 3, 4, 5 and 6 hours following activation of the device, at which point the device was removed. As shown in FIG. 20, mean calcium concentrations fell steadily throughout the period of application and reached values representing 62.5% and 66.6% of the control values at 5 and 6 hours, respectively.

EXAMPLE 3

Devices manufactured according to the present invention were used to study the delivery of insulin, heparin and salmon calcitonin to New Zealand white rabbits weighing between 2.5 kg and 3.5 kg. Hair was removed from the dorsal surface of the animal using an electric clipper twenty-fours prior to application of the device. Arterial blood samples were withdrawn for determination of plasma concentration of drug through an indwelling cannula placed in the ear artery.

Diabetes was induced in test rabbits by administration intravenously of a 150 mg/kg dose of alloxan (monohydrate) to fasted rabbits. The rabbits were provided with a dextrose solution for three days after alloxan administration and after this time normal diet was resumed. Test animals were maintained healthy with a commercial insulin preparation prior to the study. The devices were attached to the rabbits and delivery of insulin at a rate of 5 IU/h was commenced to normoglycaemic animals (for 3 hours) and to diabetic animals (for 3.25 hours). Whole blood glucose concentrations were measured using an Ames glucometer and plasma insulin concentration were measured using a RIA method. Insulin administered in this fashion resulted in considerably increased plasma insulin concentration in both normal (increased from approximately 25 fmol/ml at time 0 to approximately 275 fmol/ml at time=3h) and diabetic animals (increased from approximately 10 fmol/ml at time 0 to approximately 240 fmol/ml at time=3h). A corresponding decrease in blood glucose concentration was observed for both normal and diabetic animals.

To compare delivery of calcitonin using devices according to the present invention to conventional delivery, 40 IU calcitonin was delivered to a rabbit over 2 hours from a device according to the present invention and 20 IU calcitonin was delivered by a conventional single subcutaneous injection. In a further study, calcitonin was delivered at a rate of 25 IU/h and 100 IU/h for a period of 6 hours from devices according to the present invention. Plasma concentrations of calcium were measured using a photometric analysis while calcitonin concentrations were measured by an EIA method. Delivery of calcitonin from devices according to the present invention was found to be dose proportional and comparable to that from conventional routes.

Delivery of heparin from devices according to the present invention was studied by administering heparin at a rate of 1000 IU/h for 5 hours. Plasma heparing was assayed using an EIA method. Heparin was delivered significant anticoagulant amounts with a pharmacokinetic profile similar to that of a conventional subcutaneous injection.

While the invention has been described with respect to several preferred embodiments, it will be appreciated that these are set forth merely for purposes of example, and that many other variations, modifications and application of the invention may be made.

We claim:

1. An intradermal drug delivery device for the delivery of at least one drug to a subject via the subject's skin, comprising:
   (a) a housing having a lower surface;
   (b) a drug reservoir located with the housing;
   (c) a cover adjustable engaged with the housing from a first extended position to a second retracted position such that the cover is proximal to the lower surface of the housing when the cover is retracted and the cover is distal to the lower surface of the housing when the cover is extended;
   (d) means for affixing the cover in position with the lower surface of the housing in contact with the subject's skin;
   (e) a single hollow needle fixed to the cover and having a first end in communication with the drug reservoir and and a second end projecting outwards no further than the lower surface of the housing when the cover is extended, and to penetrate through the epidermis and into the dermis when the cover is retracted; and
   (f) means for actively discharging the drug from the reservoir to the subject's skin via the needle.

2. A device according to claim 1, wherein the device comprises a reusable electronic control unit and a disposable and replaceable cartridge unit.

3. A device according to claim 1, wherein the affixing means comprises an adhesive coating.

4. A device according to claim 1, wherein the shape of the lower surface of the housing is selected from a flat shape, a convex shape and the hollow needle extends from the centre of the convexity, a conical shape and the hollow needle extends from the apex of the cone, and a surface having a protuberance from which the needle projects.

5. A device according to claim 1, wherein the shape of the lower surface of the protective displaceable cover is selected from a flat shape, a convex shape and the hollow needle extends from the centre of the convexity, a conical shape and the hollow needle extends from the apex of the cone, and a surface having a protuberance from which the needle projects.

6. A device according to claim 1, wherein the hollow needle projects outwards from about 0.3 mm to 3.0 mm and has an outer diameter from about 0.1 mm to 0.2 mm and an inner diameter from about 0.05 mm to 0.15 mm.

7. A device according to claim 1, wherein the hollow needle projects outwards from about 0.3 mm to 5.0 mm and has an outer diameter from about 0.075 mm to 0.5 mm and an inner diameter from about 0.05 mm to 0.3 mm.

8. A device according to claim 1, wherein the drug reservoir is in the form of an expansible-contractible chamber which is expanded when filled with the drug and which can be contracted to dispense the drug therefrom.

9. A device according to claim 1, wherein the drug reservoir, when filled, has a volume from about 0.2 ml to 10.0 ml.

10. A device according to claim 9, wherein the drug reservoir has a volume from about 0.5 ml to 3.0 ml.

11. A device according to claim 1, wherein the means for actively discharging the drug comprises an electrically controlled gas generator within the housing for generating a gas to contract the drug reservoir in order to discharge the drug therefrom.

12. A device according to claim 11, wherein the gas generator is an electrolytic cell.

13. A device according to claim 11, further comprising a start button which is depressible in order to energize the gas generator and thereby to start discharging the drug from the drug reservoir.

14. A device according to claim 13, further comprising an electronic circuit for controlling the time and rate of gas generation, thereby controlling the discharge of the drug from the drug reservoir.

15. A device according to claim 14, wherein the electronic circuit comprises a microprocessor which is programmable with respect to the time and rate of gas generation.

16. A device according to claim 11, wherein the housing includes a plurality of drug reservoirs, each reservoir being contractible by a separate gas generator and communicating with an outlet cavity with which the single hollow needle also communicates.

17. A device according to claim 16, wherein all the drug reservoirs communicate in series with the outlet cavity.

18. A device according to claim 16, wherein all the drug reservoirs communicate in parallel with the outlet cavity.

19. A device according to claim 1, wherein the housing includes a plurality of drug reservoirs, each having a single hollow needle associated therewith.

20. A device according to claim 19, wherein each drug reservoir delivers a different liquid drug to the subject.

21. A device according to claim 1, wherein the housing further includes a sensor for detecting a condition in the body of the subject and for controlling the delivery of the drug in response thereto.

22. A device according to claim 21, wherein the sensor is a temperature sensor for sensing the temperature of the subject and for controlling the delivery of the drug in response thereto.

23. A device according to claim 21, wherein the sensor is a pulse rate sensor for sensing the pulse rate of the subject and for controlling the delivery of the drug in response thereto.

24. A device according to claim 21, wherein the sensor is a blood glucose sensor for sensing the blood glucose level of the subject and controlling the delivery of the drug in response thereto.

25. A device according to claim 21, wherein the sensor is a blood pressure sensor for sensing the blood pressure of the subject and controlling the delivery of the drug in response thereto.

26. A device according to claim 21, wherein the sensor is a pH sensor for sensing the pH of a body fluid of the subject and controlling the delivery of the drug in response thereto.

27. A device according to claim 8, wherein the means for actively discharging the drug comprises a spring which is stressed by the expansion of the drug reservoir upon filling it with a drug, and which tends to return to its unstressed condition to contract the reservoir and thereby to discharge the drug via the hollow needle.

28. A device according to claim 8, wherein the means for actively discharging the drug comprises a membrane which is stressed by the expansion of the drug reservoir upon filling it with a drug, and which tends to return to its unstressed condition to contract the reservoir and thereby to discharge the drug via the hollow needle.

29. A device according to claim 8, wherein the means for actively discharging the drug comprises a deformable liquid-impermeable membrane, and a rigid liquid-permeable membrane; one side of the deformable liquid-impermeable membrane defining one side of the drug reservoir; the opposite side of the deformable liquid-impermeable membrane and one side of the rigid liquid-permeable membrane defining a saline reservoir for receiving a saline solution; the opposite side of the rigid liquid-permeable membrane defining, with a rigid part of the housing, a pure water reservoir for receiving pure water to expand the saline reservoir by osmosis, thereby to contract the drug reservoir in order to dispense the drug therefrom via the hollow needle.

30. A device according to claim 1, which further comprises a membrane which is permeable to the liquid drug and impermeable to solid impurities, the membrane covering the inner end of the hollow needle.

31. A device according to claim 1, wherein the drug is selected from peptides, proteins, hormones, analgesics, anti-migraine agents, anti-coagulant agents, anti-emetic agents, cardiovascular agents, anti-hypertensive agents, narcotic antagonists, chelating agents, anti-anginal agents, chemotherapy agents, sedatives, anti-neoplastics, prostaglandins and antidiuretic agents.

32. A device according to claim 3, wherein the adhesive coating further comprises a secondary drug capable of reducing local irritation or pain.

33. A device according to claim 1, wherein the shape of the outer end of the hollow needle is selected from a bias cut, a flat cut, a conical cut, or an inverse conical cut.

34. A device according to claim 1, wherein the outer end of the hollow needle is closed and the hollow needle has an opening within 2.9 mm of the outer end.

35. A device according to claim 1, wherein the protective displaceable cover can be movably positioned so as to allow the hollow needle to project outwards from the lower surface of the cover a preselected multiplicity of different lengths when the lower surface of the cover is affixed to the subject.

36. An intradermal drug delivery device for delivering a liquid drug to a subject via the subject's skin, comprising:

(a) a housing having a lower surface;

(b) a drug reservoir within the housing, wherein the reservoir is in the form of an expansible-contractible chamber which is expanded when filled with the drug and which can be contracted to dispense the drug therefrom;

(c) a cover adjustable engaged with the housing such that the cover is proximal to the lower surface of the housing when the cover is retracted and the cover is distal to the lower surface of the housing when the cover is extended;

(e) means for affixing the cover in position with the lower surface of the cover in contact with the subject's skin;

(d) a single hollow needle associated with the drug reservoir extending through the lower surface, having an inner end communicating with the drug reservoir and an outer end projecting outwards a sufficient distance so as to extend no further than the lower surface of the housing when the cover is extended and to penetrate through the epidermis and into the dermis when the lower surface of the housing is affixed to the subject's skin and retracted; and (e) means for actively discharging the drug from the reservoir to the subject's skin via the needle.

37. A device according to claim 1, wherein the affixing means comprises an adhesive coating and the coating further comprises a secondary drug capable of reducing local irritation or pain.

38. A device according to claim 1, wherein the shape of the outer end of the hollow needle is selected from a bias cut, a flat cut, a conical cut, or an inverse conical cut.

39. A device according to claim 1, wherein the outer end of the hollow needle is closed and the hollow needle has an opening within 2.9 mm of the outer end.

40. The device of claim 1 wherein the drug is morphine.

41. The device of claim 36 wherein the drug is morphine.

* * * * *